(12) United States Patent
Zentgraf et al.

(10) Patent No.: US 6,790,940 B1
(45) Date of Patent: Sep. 14, 2004

(54) ANTIBODIES ACTIVE AGAINST A FUSION POLYPEPTIDE COMPRISING A HISTIDINE PORTION

(75) Inventors: Hanswalter Zentgraf, Heidelberg (DE); Claudia Tessmer, Schwarzach (DE); Iris Velhagen, Schwetzingen (DE); Susanne Schwinn, Hockenheim (DE); Manfred Frey, Mannheim (DE)

(73) Assignee: Deutsches Krebsforschungszentrum Stiftung des offentlichen Rechts, Heidelberg (DE)

( * ) Notice: Subject to any disclaimer, the term of this patent is extended or adjusted under 35 U.S.C. 154(b) by 0 days.

(21) Appl. No.: 08/913,139

(22) PCT Filed: Mar. 1, 1996

(86) PCT No.: PCT/DE96/00369

§ 371 (c)(1),
(2), (4) Date: Feb. 9, 1998

(87) PCT Pub. No.: WO96/26963

PCT Pub. Date: Sep. 6, 1996

(30) Foreign Application Priority Data

Mar. 1, 1995 (DE) .......................................... 195 07 166

(51) Int. Cl.[7] ............................................... C12P 21/08
(52) U.S. Cl. .................................................... 530/388.9
(58) Field of Search ........................... 530/387.1, 388.1, 530/387.9, 388.9, 389.1

(56) References Cited

U.S. PATENT DOCUMENTS 5,840,834 A * 11/1998 Peterson et al. ............ 530/323

FOREIGN PATENT DOCUMENTS

| DE | A43 39 533 | 6/1995 |
| DE | C195 07 166 | 4/1996 |
| WO | WOA94 08241 | 4/1994 |

OTHER PUBLICATIONS

Cappel Catalog #57041, Apr. 1999.*
Clinical Chemistry, vol. 27, 1797–1806, 1981.*
Janssen et al. J.B.C. vol. 270: 11222–11229, 1995.*
Randall et al. Vaccine et al., vol. 11, pp. 1247–1252, 1993.
Campbell et al., 1993, "Functional Complementation of an *Escherichia Coli* Ribonuclease H Mutation by a Cloned Genomic Fragment from the Trypanosomatid *Crithidia Fasciculata*", *Proc. Natl. Acad. Sci. U.S.A. 90*:9350–9354.
Evans et al., 1992, "Immunodetection of Recombinant Proteins Based on Antibodies Directed Against a Metal Binding Peptide Engineered for Purification by Immobilized Metal Affinity Chromatography", *Journal of Immunological Methods 156*:231–238.
Patel et al., 1995, "The Product of the UL6 Gene of Herpes Simplex Virus Type 1 is Associated with Virus Capsids", *Virology 206*:465–478.
Pederson et al., 1994, "Molecular Characterization of the AL3 Protein Encoded by a Bipartite Geminivirus", *Virology 202*:1070–1075.
Zentgraf et al., 1995, "Detection of Histidine–Tagged Fusion Proteins by Using a High–Specific Mouse Monoclonal Anti–Histidine Tag Antibody", *Nucleic Acids Res. 23*(16):3347–3348.

* cited by examiner

Primary Examiner—Patrick J. Nolan
(74) Attorney, Agent, or Firm—Dorsey & Whitney LLP; Birgit Millauer

(57) ABSTRACT

The present invention relates to an antibody active against a fusion polypeptide comprising a histidine portion, a process for the preparation thereof and its use.

1 Claim, No Drawings

US 6,790,940 B1

ANTIBODIES ACTIVE AGAINST A FUSION POLYPEPTIDE COMPRISING A HISTIDINE PORTION

This is a national phase filing of the Application No. PCT/DE96/00369, which was filed with the Patent Corporation Treaty on Mar. 1, 1996, and is entitled to priority of the German Patent Application P 195 07 166.2, filed Mar. 1, 1995.

I. FIELD OF THE INVENTION

The present invention relates to antibodies which are active against a fusion polypeptide comprising a histidine portion, a process for the preparation thereof and their use.

II. BACKGROUND OF THE INVENTION

It is known to express a polypeptide in the form of a histidine fusion polypeptide. In such a polypeptide, a histidine portion of, e.g., 6–18 successive histidine residues is fused to the C- or N-terminus of the polypeptide. Hence it is possible to isolate the histidine fusion polypeptide by means of a nickel-chelate chromatographic column from the supernatant or cell lysate of the cell expressing it.

However, the above column is expensive. Furthermore, its use costs a lot of time. Therefore, it is not suited for the rapid detection of the expression of a histidine fusion polypeptide. But such a detection is necessary, particularly when it is the objective to screen large numbers of cells.

Thus, it is the object of the present invention to provide means by which the expression of a histidine fusion polypeptide can be detected rapidly.

III. SUMMARY OF THE INVENTION

The present invention relates to an antibody active against a fusion polypeptide comprising a histidine portion, a process for the preparation thereof and its use.

IV. DETAILED DESCRIPTION OF THE INVENTION

It is the object of the present invention to provide means by which the expression of a histidine fusion polypeptide can be detected rapidly.

According to the invention this is achieved by an antibody which is directed against a fusion polypeptide comprising a histidine portion.

Such an antibody may be a polyclonal or monoclonal antibody, a monoclonal antibody being preferred. The antibody may be obtained from any animal or human being, rabbits being preferred for a polyclonal antibody and mice being preferred for a monoclonal antibody.

In addition, the antibody may be synthetic, portions which are not necessary for the above-mentioned identification optionally lacking fully or partially therefrom and these portions being replaced by others which give the antibody further favorable properties, respectively.

The expression "fusion polypeptide comprising a histidine portion" comprising a polypeptide (peptide) of any kind and length which has a histidine portion. Such a polypeptide may be expressed by any cells, e.g., bacteria, yeasts, cells of insects, plants and animals, as well as organisms, e.g., transgenic animals. An above histidine portion may comprise, e.g., 6–18, preferably 6, successive histidine residues and be fused to the N and/or C terminus of the polypeptide.

A preferred antibody of the present invention, namely a monoclonal mouse antibody having the above identification, was deposited under No. ACC 2207 with the DSM (Deutsche Sammlung von Mikroorganismen und Zellkulturen GmbH (German-type collection of microorganisms), Mascheroder Weg 1b, D-38124, Braunschweig, Germany) on Feb. 15, 1995.

Antibodies according to the invention can be prepared according to conventional methods. If polyclonal antibodies and monoclonal antibodies, respectively, are to be prepared, it will be favorable to immunize animals, particularly rabbits for the former antibodies and mice for the latter antibodies, with an above histidine fusion polypeptide, e.g., His p53 (see, German patent application P 42 32 823.3) or His hdm2 (see, German patent application P 43 39 553.3), preferably a mixture thereof. The animals can be further boostered with the same histidine fusion polypeptide or peptides. Other histidine fusion polypeptides or a combination of these and the preceding histidine fusion polypeptide or polypeptides may also be used for boostering. The polyclonal antibodies may then be obtained from the serum of the animals. Spleen cells of the animals are fused with myeloma cells for the monoclonal antibodies.

For the preparation of synthetic antibodies, e.g., the above-obtained monoclonal antibodies may be used as a basis. For this purpose, it is the obvious thing to analyze the antigen-binding region of the monoclonal antibodies and identify the portions which are necessary and not necessary for the above identification. The necessary portions may then be modified and the non-necessary portions can be fully or partially eliminated and replaced by portions giving the antibodies further favorable properties, respectively. Also, portions can be modified, eliminated or replaced beyond the binding regions of the antibodies. A person skilled in the art knows that particularly the DNA recombination technology is suitable for the above measures. He is perfectly familiar therewith.

Antibodies according to the invention distinguish themselves in that they recognize any fusion polypeptides comprising a histidine portion. Therefore, the antibodies are suitable for the rapid detection of the expression of such fusion polypeptides. This may be carried out in any detection methods, particularly in a Western blot, an ELISA, an immunoprecipitation or an immunofluorescence. For this purpose, the antibodies according to the invention may be labeled, if appropriate, or used in combination with labeled antibodies directed thereagainst.

The blow examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

V. EXAMPLES

A. Example 1

Preparation of Monoclonal Antibodies

Mice were used for immunization. His hdm2 (amino acid 1-284), His hdm2 (amino acid 58491) and His p53 (amino acid 66-393) (see, supra) were used as antigens. They were dissolved in a buffer comprising 8 M urea, 100 mM $NaH_2PO_4$, 10 mM Tris-HCl.

| Immunization And Booster Pattern: | | |
|---|---|---|
| Day 1: | 50 µl | (= 10 µg) His hdm2 (amino acid 1–284) |
| | 50 µl | (= 10 µg) His hdm2 (amino acid 58–491) |
| | 50 µl | PBS (phosphate-buffered saline) |
| | 150 µl | Freund's adjuvant complete |
| | 300 µl | mix |
| | 200 µl | of the mix were injected into a mouse |
| Day 30: | 50 µl | (= 10 µg) His hdm2 (amino acid 1–284) |
| | 50 µl | (= 10 µg) His hdm2 (amino acid 58–491) |
| | 20 µl | PBS |
| | 120 µl | Freund's adjuvant incomplete |
| | 240 µl | mix |
| | 200 µl | of the mix were injected into the above mouse. |
| Day 60: | 50 µl | (= 10 µg) His hdm2 (amino acid 1–284) |
| | 50 µl | (= 10 µg) His hdm2 (amino acid 58–491) |
| | 85 µl | PBS |
| | 115 µl | Freund's adjuvant incomplete |
| | 300 µl | mix |
| | 200 µl | of the mix were injected into the above mouse. |
| Day 90: | 50 µl | (= 10 µg) His hdm2 (amino acid 1–284) |
| | 50 µl | (= 10 µg) His hdm2 (amino acid 58–491) |
| | 200 µl | PBS |
| | 300 µl | mix |
| | 200 µl | of the mix were injected into the above mouse. |
| Day 180: | 150 µl | (= 20 µg) His p53 (amino acid 66–393) |
| | 150 µl | Freund's adjuvant complete |
| | 300 µl | mix |
| | 200 µl | of the mix were injected into the above mouse. |
| Day 230: | 75 µl | (= 10 µg) His p53 (amino acid 66–393) |
| | 25 µl | (= 5 µg) His hdm2 (amino acid 1–284) |
| | 25 µl | (= 5 µg) His hdm2 (amino acid 58–491) |
| | 125 µl | Freund's adjuvant incomplete |
| | 250 µl | mix |
| | 200 µl | of the mix were injected into the above mouse. |
| Day 260: | 75 µl | (= 10 µg) His p53 (amino acid 66–393) |
| | 25 µl | (= 5 µg) His hdm2 (amino acid 1–284) |
| | 25 µl | (= 5 µg) His hdm2 (amino acid 58–491) |
| | 125 µl | PBS |
| | 250 µl | mix |
| | 200 µl | of the mix were injected into the above mouse. |

The mouse was killed on day 262. Spleen cells were removed therefrom and fused with myeloma cells. Monoclonal antibodies were obtained. One of them was deposited under ACC 2207 with DSM on Feb. 15, 1995.

B. Example 2

Preparation of Polyclonal Antibodies

Rabbits were used for immunization. The antigens of Example 1 were employed. The immunization and booster pattern was identical with that of Example 1 up to day 90 inclusive.

Day 92: 5 ml of blood were removed from the rabbit's auricular vein and tested for antibody activity in an ELISA and Western blot, respectively.
Day 93: Following a positive test on day 92, the animals were killed and the antibodies were obtained from the serum.

C. Example 3

Detection of Histidine Fusion Polypeptides by Antibodies According to the Invention (a) Western Blot. Histidine fusion polypeptides, namely His hdm2 (amino acid 1-284), His hdm2 (amino acid 58-491) and His p53 (amino acid 66-393) of Example 1, as well as the polypeptides hdm2 (amino acid 1-284), WAF 1 (=wild type-activating factor) and t16 (=cell-regulating protein) as control were subjected to a polyacrylamide gel electrophoresis. The gel was transferred overnight to a nitrocellulose membrane. It was then incubated with the above antibody ACC 2207 diluted in a ratio of 1:10 and 1:50, respectively, at 37° C. for 1 hour. After several wash steps using PBS (0.05% Tween 20), a purchasable alkaline phosphatase-coupled goat-anti-mouse antibody (dilution according to the manufacturer's indication) was added. A 30-minute incubation at 37° C. was followed by several wash steps using PBS and thereafter the alkaline phosphatase detection reaction with alkaline phosphatase including developing solution (36 µM 5'-bromo-4-chloro-3-indolyphosphate, 400 µM nitroblue tetrazolium, 100 mM Tris-HCl, pH 9.5, 100 mM NaCl, 5 mM $MgCl_2$) at room temperature until bands were visible.

It showed that the antibody ACC 2207 according to the invention recognizes specifically histidine fusion polypeptides but not polypeptides without histidine portion.

(b) ELISA. A 96-well plate was provided per well with 100 µl each, which included 20 ng and 8 ng, respectively, of the histidine fusion polypeptides and the controls of (a), respectively. After incubation at 4° C. overnight, 3 short wash steps using PBS followed. Thereafter, the free binding sites of the polymeric carrier were blocked by one-hour incubation using 1% BSA in PBS at 37° C. The antibody ACC 2207 according to the invention which was diluted in a ratio of 1:10 and 1:50, respectively, was incubated on the plate at 37° C. for 1 hour. After 8 wash steps using PBS, the peroxidase-coupled goat anti-mouse antibody of (a) was added. A 30-minute incubation at 37° C. was followed by 8 wash steps and thereafter the peroxidase detection reaction with developing solution (50 mM sodium acetate, 0.4 mM 3,3',5,5"-tetramethylbenzidine dihydrochloride, 4.4 mM $H_2O_2$) at room temperature until bands were visible.

It showed that the antibody ACC 2207 according to the invention recognizes specifically histidine fusion polypeptides but not a polypeptide without histidine portion.

All references cited within the body of the instant specification are hereby incorporated by reference in their entirety.

What is claimed is:

1. An antibody, wherein said antibody is produced by a hybridoma deposited under ACC 2207 with the Deutsche Sammlung von Mikroorganismen und Zellkulturen GmbH (DSM).

* * * * *